US012709777B1

(12) United States Patent
Chaudhuri et al.

(10) Patent No.: US 12,709,777 B1
(45) Date of Patent: Aug. 18, 2026

(54) METHOD TO RISK-STRATIFY OLIGOMETASTATIC NON-SMALL CELL LUNG CANCER PATIENTS USING CELL-FREE DNA LIQUID BIOPSIES

(71) Applicant: Washington University, St. Louis, MO (US)

(72) Inventors: Aadel Chaudhuri, St. Louis, MO (US); Nicholas Semenkovich, St. Louis, MO (US)

(73) Assignee: Washington University, St. Louis, MO (US)

( * ) Notice: Subject to any disclaimer, the term of this patent is extended or adjusted under 35 U.S.C. 154(b) by 400 days.

(21) Appl. No.: 18/529,866

(22) Filed: Dec. 5, 2023

Related U.S. Application Data

(60) Provisional application No. 63/386,126, filed on Dec. 5, 2022.

(51) Int. Cl.
*C12Q 1/6886* (2018.01)
*C12Q 1/6874* (2018.01)

(52) U.S. Cl.
CPC ......... *C12Q 1/6886* (2013.01); *C12Q 1/6874* (2013.01); *C12Q 2600/106* (2013.01); *C12Q 2600/156* (2013.01)

(58) Field of Classification Search
CPC ................ C12Q 1/6886; C12Q 1/6874; C12Q 2600/106; C12Q 2600/156
See application file for complete search history.

(56) References Cited

U.S. PATENT DOCUMENTS 9,291,625 B2 3/2016 Semizarov et al.
9,297,045 B2 3/2016 Semizarov et al.
2019/0256924 A1 8/2019 Vogelstein et al.
2021/0109086 A1 4/2021 Kuhn et al.
2021/0398617 A1 12/2021 Finkle et al.

FOREIGN PATENT DOCUMENTS

WO WO-2022155587 A2 * 7/2022 ........... C12Q 1/6806

OTHER PUBLICATIONS

Heitzer et al. Recommendations for a practical implementation of circulating tumor DNA mutation testing in metastatic non-small-cell lung cancer. ESMO Open, vol. 7, Issue 2, No. 100399, pp. 1-12 (2022).

Yang et al. T (2021) Application of Circulating Tumor DNA as a Biomarker for Non-Small Cell Lung Cancer. Front. Oncol., vol. 11, No. 725938, pp. 1-9. doi: 10.3389/fonc.2021.725938.

Low et al. Rapid genomic profiling of circulating tumor DNA in non-small cell lung cancer using Oncomine Precision Assay with Genexus™ integrated sequencer. Transl Lung Cancer Res, 2022, vol. 11, No. 5, pp. 711-721. https://dx.doi.org/10.21037/tlcr-21-981.

* cited by examiner

*Primary Examiner* — Cynthia B Wilder

(57) ABSTRACT

Among the various aspects of the present disclosure is the provision of a method to risk-stratify cancer patients using circulating DNA assays. In other aspects, a method of selecting treatment for an early-stage non-small cell lung cancer for a patient in need that includes subjecting a blood sample from a patient to a liquid biopsy assay to identify at least one circulating tumor DNA (ctDNA) variant indicative of oligometastatic disease, and selecting a systemic therapy as a treatment if the liquid biopsy assay identifies the at least one ctDNA variant, or selecting a radiation therapy if the liquid biopsy assay identifies essentially zero ctDNA variants.

11 Claims, 19 Drawing Sheets

| Characteristic | Entire Cohort ($n$ = 1487) | Sub-cohort ($n$ = 309) |
|---|---|---|
| Age, mean (SD), y | 64.7 (10.1) | 63.1 (10.1) |
| Sex | | |
| Male | 703 (47.3%) | 149 (48.2%) |
| Female | 784 (52.7%) | 160 (51.8%) |
| Race and ethnicity | | |
| Asian | 93 (6.3%) | 20 (6.5%) |
| Black | 150 (10.1%) | 38 (12.3%) |
| White | 835 (56.1%) | 176 (57.0%) |
| Other | 44 (3.0%) | 11 (3.5%) |
| Unknown | 365 (24.5%) | 64 (20.7%) |
| Primary Tumor Histology | | |
| Adenocarcinoma | 1078 (72.5%) | 233 (75.4%) |
| Squamous | 267 (18.0%) | 50 (16.2%) |
| Other/Not Specified | 142 (9.5%) | 26 (8.4%) |
| Initial Reported Stage | | |
| Not Reported | 51 (3.4%) | 1 (0.3%) |
| Stage 0 | 1 (0.1%) | 0 (0.0%) |
| Stage I | 87 (5.8%) | 9 (2.9%) |
| Stage II | 70 (4.7%) | 4 (1.3%) |
| Stage III | 272 (18.3%) | 34 (11.0%) |
| Stage IV | 1006 (67.7%) | 261 (84.5%) |
| Driver Gene Alterations (Pre-Liquid Biopsy) | | |
| *EGFR* | 251 (16.9%) | 53 (17.2%) |
| *ALK* | 50 (3.4%) | 9 (2.9%) |
| *ROS1* | 21 (1.4%) | 2 (0.6%) |
| *MET* | 25 (1.7%) | 8 (2.6%) |
| *RET* | 7 (0.5%) | 1 (0.3%) |
| *BRAF* | 36 (2.4%) | 9 (2.9%) |
| *KRAS* | 72 (4.8%) | 16 (5.2%) |
| *ERBB2* | 14 (0.9%) | 3 (1.0%) |
| Metastatic organ systems, mean[a] (SD, range) | 1.3 (0.64, 1–8) | 1.3 (0.56, 1–5) |
| PD-L1 Status[b] | | |
| Positive | 302 (20.3%) | 59 (19.1%) |
| Negative | 202 (13.6%) | 48 (15.5%) |
| Unknown | 983 (66.1%) | 202 (65.4%) |
| Smoking Status | | |
| Current/Former Smoker | 1006 (67.7%) | 221 (71.5%) |
| Never Smoker | 323 (21.7%) | 73 (23.6%) |
| Unknown | 158 (10.6%) | 15 (4.9%) |
| Documented Radiotherapy | 975 (66%) | 309 (100%) |
| Reported Lines of Therapy | | |
| Not Reported | 212 (14.3%) | 34 (11.0%) |
| 1 | 674 (45.3%) | 128 (41.4%) |
| 2 | 374 (25.1%) | 93 (30.1%) |
| 3 | 141 (9.5%) | 33 (10.7%) |
| ≥4 | 86 (5.8%) | 21 (6.8%) |

FIG. 3

| Characteristic | Entire Cohort | Sub-cohort |
|---|---|---|
| Liquid biopsies performed | 1880 | 434 |
| Variants detected (mean per ctDNA test) | 38,546 (20.5) | 9069 (20.9) |
| Pathogenic/likely pathogenic | 3503 (9.1%) | 828 (9.1%) |
| Conflicting evidence | 17 (0.04%) | 10 (0.11%) |
| Benign/likely benign | 30,911 (80.2%) | 7254 (80.0%) |
| Uncertain significance | 4115 (10.7%) | 977 (10.8%) |
| Driver gene alterations detected | | |
| *EGFR* | 94 | 15 |
| *ALK* | 9 | 1 |
| *ROS1* | 6 | 0 |
| *MET* | 11 | 4 |
| *RET* | 3 | 2 |
| *BRAF* | 11 | 0 |
| *KRAS* | 64 | 11 |
| *ERBB2* | 13 | 5 |

FIG. 4

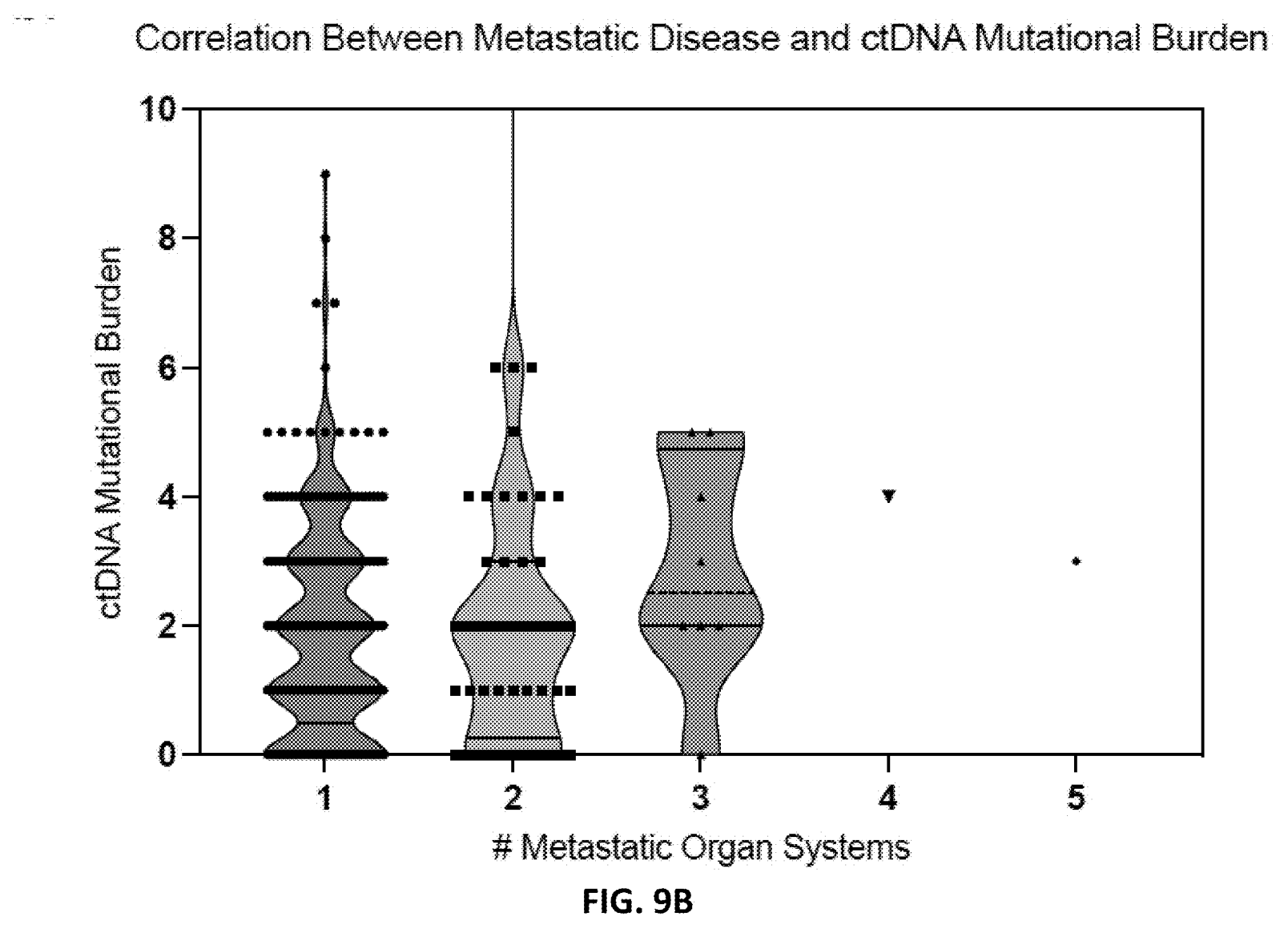

Correlation Between Metastatic Disease and ctDNA Mutational Burden ctDNA Mutational Burden 10
8
6
4
2
0

1
2
3
4
5

Metastatic Organ Systems

FIG. 9B

METHOD TO RISK-STRATIFY OLIGOMETASTATIC NON-SMALL CELL LUNG CANCER PATIENTS USING CELL-FREE DNA LIQUID BIOPSIES

CROSS-REFERENCE TO RELATED APPLICATIONS

This application claims priority from U.S. Provisional Application Ser. No. 63/386,126 filed on Dec. 5, 2022, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to methods to risk-stratify cancer patients using cell-free DNA liquid biopsies.

BACKGROUND OF THE INVENTION

Early-stage non-small cell lung cancer (NSCLC) is frequently curable with aggressive local treatment using stereotactic body radiotherapy (RT). While patients with widespread metastatic disease are currently incurable, some patients with more limited (oligometastatic) disease can experience prolonged periods of progression-free survival or even cure with locally aggressive RT. However, it is challenging to determine which oligometastatic NSCLC patients will benefit from this emerging RT-based paradigm versus those who should be prioritized for systemic therapy. Plasma circulating tumor DNA (ctDNA) has been shown to be powerfully prognostic in the post-RT setting for localized NSCLC.

SUMMARY OF THE INVENTION

Among the various aspects of the present disclosure is the provision of a method of selecting a treatment for an early-stage non-small cell lung cancer for a patient in need that includes providing a blood sample from the patient prior to radiation therapy (RT), subjecting the blood sample to a liquid biopsy assay configured to detect at least one circulating tumor DNA (ctDNA) variant indicative of oligometastatic disease, and selecting a systemic therapy as a treatment if the liquid biopsy assay identifies the at least one ctDNA variant and otherwise selecting a radiation therapy as the treatment. In some aspects, the at least one circulating tumor DNA (ctDNA) variant indicative of oligometastatic disease is selected from an oncogenic mutation variant, a resistance mutation variant, and any combination thereof. In some aspects, the at least one oncogenic mutation variant, resistance mutation variant, and any combination thereof is selected from a single nucleotide variant (SNVs), an insertion/deletion (indel), a rearrangement, a copy number variation (CNV), and a microsatellite instability (MSI). In some aspects, the at least one circulating tumor DNA (ctDNA) variant is identified within at least one gene selected from EGFR, ALK, ROS1, MET, RET, BRAF, KRAS, ERBB2, and any combination thereof. In some aspects, the method further includes quantifying the maximum variant allele frequency (VAF) in the patient based on the at least one circulating tumor DNA (ctDNA) variant detected by the liquid biopsy assay.

In another aspect, a method of selecting a treatment for an early-stage non-small cell lung cancer for a patient in need is disclosed that includes providing a blood sample from the patient prior to radiation therapy (RT), subjecting the blood sample to a liquid biopsy assay configured to detect at least one circulating tumor DNA (ctDNA) variant indicative of oligometastatic disease, quantifying a maximum variant allele frequency (VAF) in the patient based on the at least one circulating tumor DNA (ctDNA) variant detected by the liquid biopsy assay based on the at least one circulating tumor DNA (ctDNA) variant identified by the liquid biopsy assay, and selecting a systemic therapy as a treatment if the maximum VAF value falls above a threshold VAF value and otherwise selecting a radiation therapy as the treatment. In some aspects, the threshold maximum VAF value is zero. In some aspects, the threshold maximum VAF value is 0.1. In some aspects, the at least one circulating tumor DNA (ctDNA) variant indicative of oligometastatic disease is selected from an oncogenic mutation variant, a resistance mutation variant, and any combination thereof. In some aspects, the at least one oncogenic mutation variant, resistance mutation variant, and any combination thereof is selected from a single nucleotide variant (SNVs), an insertion/deletion (indel), a rearrangement, a copy number variation (CNV), and a microsatellite instability (MSI). In some aspects, the at least one circulating tumor DNA (ctDNA) variant is identified within at least one gene selected from EGFR, ALK, ROS1, MET, RET, BRAF, KRAS, ERBB2, and any combination thereof.

DESCRIPTION OF THE DRAWINGS

Those of skill in the art will understand that the drawings, described below, are for illustrative purposes only. The drawings are not intended to limit the scope of the present teachings in any way.

FIG. 3 is a table summarizing cohort characteristics for the patient population sampled as described in the examples herein.

FIG. 4 is a table of the genomic alterations detected in cell-free DNA as described in the examples herein.

FIG. 9B is a graph of a correlative analysis between pre-RT ctDNA and metastatic burden (represented by the number of metastatic organ systems). No significant correlation was identified between the pre-RT ctDNA mutational burden assayed by the number of pathogenic or likely pathogenic variants (P=0.32, R2=0.015 by one-way ANOVA).

DETAILED DESCRIPTION OF THE INVENTION

Oligometastatic non-small cell lung cancer (NSCLC) patients may uniquely benefit from personalized therapies via liquid biopsy. Widespread metastatic disease is incurable, yet some patients with oligometastatic disease experience prolonged progression-free survival (PFS) when treated with aggressive local stereotactic body radiotherapy (RT). Distinguishing patients who would benefit from aggressive RT from those who would benefit from systemic therapies remains a challenge. It is hypothesized that pre-RT ctDNA can be used to risk-stratify those with oligometastatic NSCLC and enable earlier personalized approaches when considering systemic therapy versus aggressive local RT.

The present disclosure is based, at least in part, on the discovery that ctDNA can serve as a valuable pre-RT biomarker for risk-stratifying oligometastatic NSCLC patients, with the potential to personalize the selection of RT versus systemic therapy decision-making. As shown herein, methods to risk stratify cancer patients using ctDNA assays are described.

One aspect of the present disclosure provides methods to risk-stratify cancer patients using ctDNA assays. Another aspect of the present disclosure provides methods of selecting a treatment for an early-stage non-small cell lung cancer (NSCLC) that includes selecting a radiation therapy if a liquid assay of a patient's blood sample detects essentially zero circulating tumor DNA variants indicative of NSCLC, or selecting a systemic therapy of the liquid assay detects at least one ctDNA variant.

Figure 11:
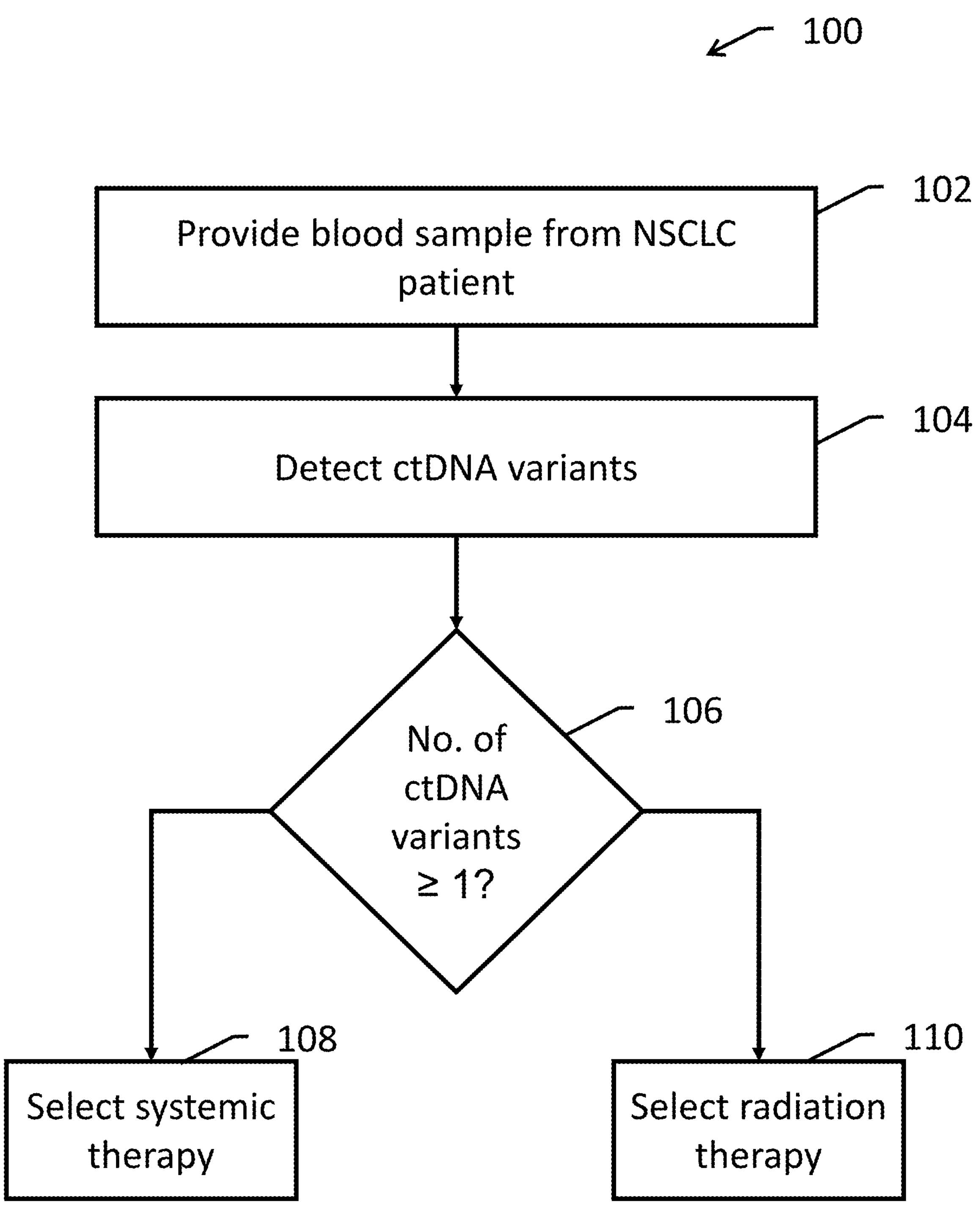
FIG. 11 is a flow chart illustrating a method of selecting a treatment for an NSCLC patient in accordance with one aspect of the disclosure.

FIG. 11 is a flow chart summarizing the steps of a method 100 for identifying a treatment for an NSCLC patient in one aspect. The method 100 includes providing a blood sample from the NSCLC patient at 102. In some aspects, the NSCLC patient has been identified as having a form of NSCLC including, but not limited to oligometastatic NSCLC. Oligometastatic NSCLC cancer refers to NSCLC that is metastatic but with a few sites of metastasis, as opposed to widely metastatic NSCLC with many sites of metastasis. In some aspects, the patient may be untreated or may be receiving a systemic treatment. The systemic treatment may be any suitable systemic treatment known in the art including, but not limited to, chemotherapy, immunotherapy, and gene therapy.

Referring again to FIG. 11, the method 100 further includes detecting ctDNA variants in the blood sample at 104. In some aspects, detecting the ctDNA variants includes separating the ctDNA from the blood sample and detecting the ctDNA variants. In some aspects, separating the ctDNA from the blood sample and detecting the ctDNA variants may be accomplished in separate processes, or may be accomplished in a combined process. Detecting the ctDNA variants may be performed using any suitable known liquid biopsy method including, but not limited to, a Tempus XF assay (v2).

In some aspects, any suitable existing kit can be used to extract cfDNA from the blood sample. In some aspects, any suitable NGS tool and/or bioinformatics tool can be used to detect ctDNA variants.

In various aspects, ctDNA variants detected at 104 may include oncogenic mutation variants associated with the ontogeny of NSCLC, resistance mutation variants associated with the resistance to treatments, and any combination thereof. Non-limiting examples of detected ctDNA variants include single nucleotide variants (SNVs), insertions/deletions (indels), rearrangements, copy number variations (CNVs), and microsatellite instabilities (MSIs).

Any suitable method of detecting and analyzing the ctDNA variants may be used without limitation. Non-limiting examples of suitable methods to identify fusions in the ctDNA include SpeedSeq. Non-limiting examples of suitable methods to identify CNVs in the ctDNA include CNVkit. Non-limiting examples of suitable methods to analyze ctDNA results for variants include VarDict.

Without being limited to any particular theory, the ctDNA variants may be characterized as pathogenic or likely pathogenic based on their predicted functional impact and clinical evidence. In some aspects, the functional impact of the ctDNA variants may be predicted using any suitable method including, but not limited to, SnpEff.

In some aspects, the ctDNA variants detected at 104 may be within driver genes associated with the ontogeny of NSCLC or metastasizing thereof. Non-limiting examples of suitable driver genes include EGFR, ALK, ROS1, MET, RET, BRAF, KRAS, ERBB2, and any combination thereof.

In some aspects, if ctDNA is detectable, then systemic treatment can be strengthened and escalated. In another aspect, if there is no (or low) detectable ctDNA in the assays described in the present disclosure, then systemic treatment can be forgone in favor of consolidative radiotherapy.

Referring again to FIG. 11, the number of ctDNA variables is analyzed at 106 to formulate a recommendation for a suitable therapy. As illustrated in FIG. 11, if the number of detected ctDNA variants is greater than 1, then a systemic therapy is identified at 108, or otherwise a radiation therapy is identified at 110. Non-limiting examples of radiation therapy (RT) include a locally aggressive RT, a locally consolidative RT, and/or a locally ablative RT.

In some aspects, if the patient is already receiving a systemic therapy, selecting radiation therapy at 110 may include terminating the existing systemic therapy. In some aspects, if the patient is already receiving a systemic therapy, selecting systemic therapy at 108 may include strengthening and/or escalating the existing systemic therapy.

Figure 12:
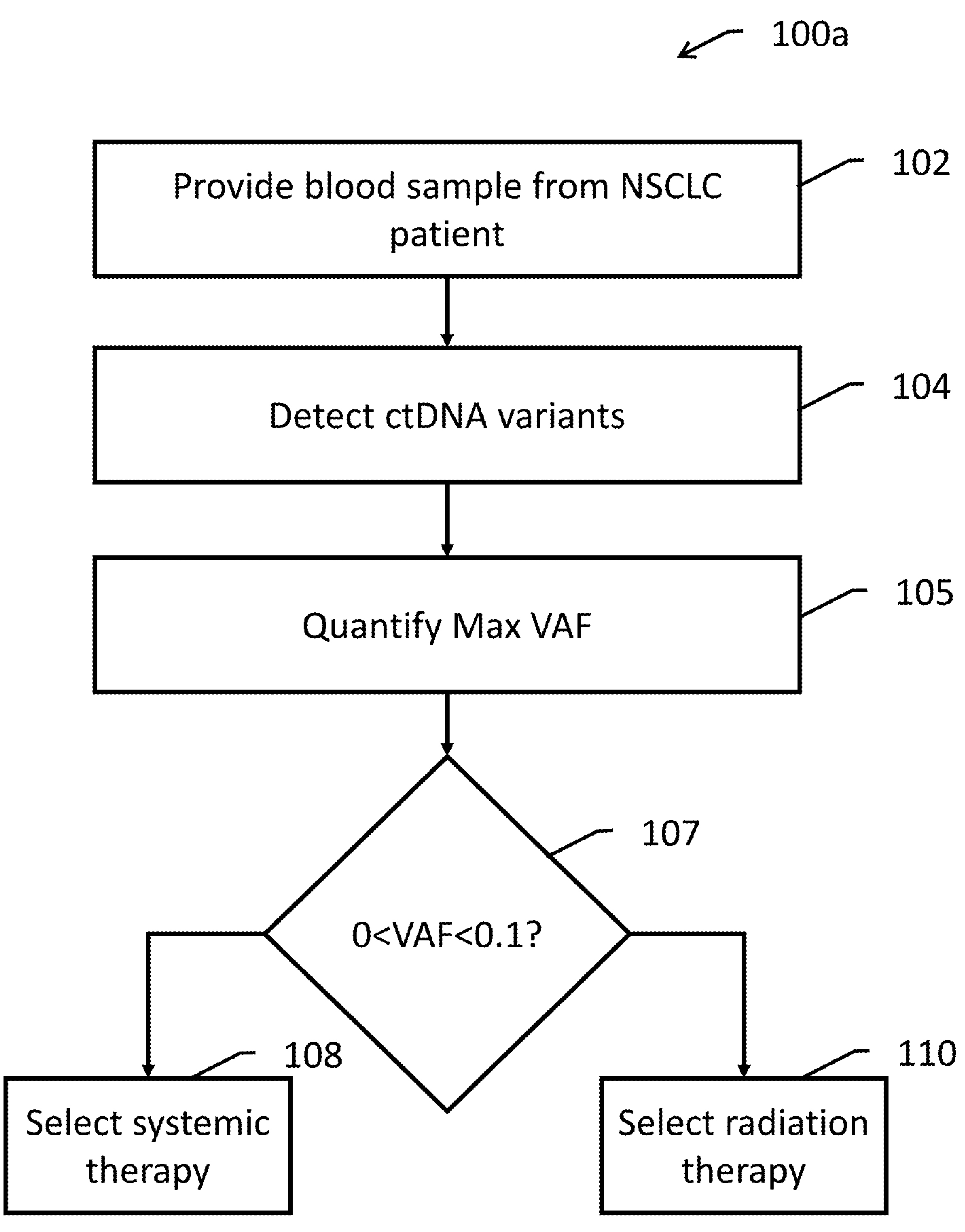
FIG. 12 is a flow chart illustrating a method of selecting a treatment for an NSCLC patient in accordance with another aspect of the disclosure.

In various other aspects, shown illustrated in FIG. 12, the method 100*a* may include quantifying a maximum variant allele frequency (max VAF) at 105. In some aspects, a mean variant allele frequency (mean VAF) may be quantified. The method 100*a* further includes selecting a treatment based on the max VAF at 107. If the max VAF is greater than zero, a systemic therapy is selected at 108, and otherwise a radiation therapy is selected at 110.

In various aspects, the predicted risk of the non-small cell lung cancer patient may be stratified granularly based on the number of pathogenic ctDNA variants detected prior to receiving radiotherapy (pre-RT). In some aspects, the patients are predicted to be at higher risk, with significantly reduced progression-free survival (PFS) and overall survival (OS) when 1-3 ctDNA variants are identified, and even lower PFS and OS when greater than 4 ctDNA variants are identified relative to patients with no ctDNA variants identified using the disclosed methods.

In various aspects, the predicted risk of the non-small cell lung cancer patient may be stratified granularly based on the maximum number of variant allele frequencies prior to receiving radiotherapy (pre-RT). In some aspects, the patients are predicted to be at higher risk, with significantly reduced progression-free survival (PFS) and overall survival (OS) when the max VAF is between 0 and 0.1, and even lower PFS and OS when max VAF is is at least 0.1 relative to patients with no ctDNA variants (and VAF=0) identified using the disclosed methods.

A control sample or a reference sample as described herein can be a sample from a healthy subject. A reference value can be used in place of a control or reference sample, which was previously obtained from a healthy subject or a group of healthy subjects. A control sample or a reference sample can also be a sample with a known amount of a detectable compound or a spiked sample.

The methods and algorithms of the invention may be enclosed in a controller or processor. Furthermore, methods and algorithms of the present invention can be embodied as a computer-implemented method or methods for performing such computer-implemented method or methods, and can also be embodied in the form of a tangible or non-transitory computer-readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer programs include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10:

0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1—Pre-Radiotherapy CtDNA Risk-Stratifies Non-Small Cell Lung Cancer (NSCLC) Patients with Oligometastatic Disease To develop and validate a method of risk-stratifying non-small lung cell cancer patients with oligometastatic disease based on the analysis of ctDNA liquid biopsy assay results, the following experiments were conducted.

BACKGROUND

Oligometastatic non-small cell lung cancer (NSCLC) patients may uniquely benefit from personalized therapies via liquid biopsy. Widespread metastatic disease is incurable, yet some patients with oligometastatic disease experience prolonged progression-free survival when treated with aggressive local stereotactic body radiotherapy (RT). Distinguishing patients who would benefit from aggressive RT from those who would benefit from systemic therapies remains a challenge. It was hypothesized that pre-RT ctDNA can be used to risk-stratify those with oligometastatic NSCLC and enable earlier personalized approaches when considering systemic therapy versus aggressive local RT.

Methods

A retrospective multi-institutional cohort of 1,487 patients (median age: 65 years, 53% female [n=784], 47% male [n=703]) who were diagnosed with oligometastatic NSCLC was selected. Each patient underwent liquid biopsy ctDNA analysis using the Tempus XF assay (v2) at least once, with a subset of patients undergoing serial sampling at 2-8 time points for a total of 1,880 ctDNA assays. 309 of the patients (20%) underwent RT after liquid biopsy was obtained and oligometastatic NSCLC was diagnosed. Outcomes for overall survival (OS) and progression-free survival (PFS) were defined with respect to the initiation time of RT (i.e., time from RT to death, time from RT to progressive disease).

Results

Across all ctDNA assays, 3,520 pathogenic or likely pathogenic (P/LP) variants were identified (1.8 variants/sample, mean). Among patients with a liquid biopsy obtained prior to RT, 48% (n=151) experienced progressive disease and 11% (n=34) died during the study period. Focusing on patients with ctDNA obtained pre-RT, P/LP variants were detected in 74% (n=230) while 26% (n=79) had zero variants detected. Of those with detectable variants, 76% (n=175) had 1-3 variants, while 24% (n=55) had ≥4 P/LP variants detected in ctDNA. Both overall survival and progression-free survival were significantly worse in patients with detectable ctDNA from pre-RT liquid biopsy compared to those without (median OS 16.8 months vs. 25 months; p=0.027, HR=1.65; median PFS 5.4 months vs. 8.8 months; p=0.021, HR=1.57). Remarkably, survival correlated inversely with the number of detected variants from pre-RT liquid biopsies; when patients were stratified by variant quantity, both OS and PFS were significant (OS p=0.045, PFS p=0.003; stratified by 0, 1-3, and ≥4 variants). This finding was also significant in a multivariate Cox proportional hazards analysis (OS HR=1.15, CI 1.04-1.24; PFS HR=1.16, CI 1.06-1.25), but was not significant for parameters such as age at diagnosis or squamous histology.

Conclusions

These data suggest that a ctDNA-informed approach may be a powerful pre-RT biomarker to help risk-stratify oligometastatic NSCLC patients and potentially enable personalized decision-making for RT versus systemic therapy.

Example 2—Pre-Radiotherapy ctDNA Analysis can Precisely Risk-Stratify Oligometastatic Non-Small Cell Lung Cancer Patients This is another example that describes how pre-radiotherapy ctDNA analysis can precisely risk-stratify oligometastatic non-small cell lung cancer patients.

BACKGROUND

Early-stage non-small cell lung cancer (NSCLC) is frequently curable with aggressive local treatment using stereotactic body radiotherapy. While patients with widespread metastatic disease are currently incurable, some patients with more limited (oligometastatic) disease can experience prolonged periods of progression-free survival or even cure with locally aggressive RT. However, it is challenging to determine which oligometastatic NSCLC patients will benefit from this emerging RT-based paradigm versus those who should be prioritized for systemic therapy. Plasma circulating tumor DNA (ctDNA) has been shown to be powerfully prognostic in the post-RT setting for localized NSCLC. ctDNA analysis could be similarly leveraged to risk-stratify patients with oligometastatic NSCLC to enable more personalized selection of RT versus systemic therapy.

Objectives

To risk-stratify oligometastatic NSCLC patients using pre-RT ctDNA with the goal of personalizing RT versus systemic therapy decision-making.

Methods

A multi-institutional retrospective cohort of 1,487 patients diagnosed with oligometastatic NSCLC was analyzed. Every patient in the study underwent plasma liquid biopsy ctDNA analysis using the Tempus XF assay (v2). A total of 1,880 ctDNA assays were performed; all 1,487 NSCLC patients had at least one ctDNA assay performed with select patients having 2-8 serial blood samples analyzed for ctDNA. ctDNA assay results were filtered for pathogenic or likely pathogenic variants, queried for detection status, and additionally analyzed for mean and maximum variant allele frequency (VAF). Of the 1,487 patients in the cohort, 309 (20%) underwent radiation therapy after liquid biopsy testing was performed and oligometastatic NSCLC was diagnosed. Both overall survival (OS) and progression-free survival (PFS) were computed with respect to initiation of RT (i.e., time from RT to death, time from RT to progressive disease). Statistical analyses were performed using Apache Superset and GraphPad Prism.

Results

Figure 1A:
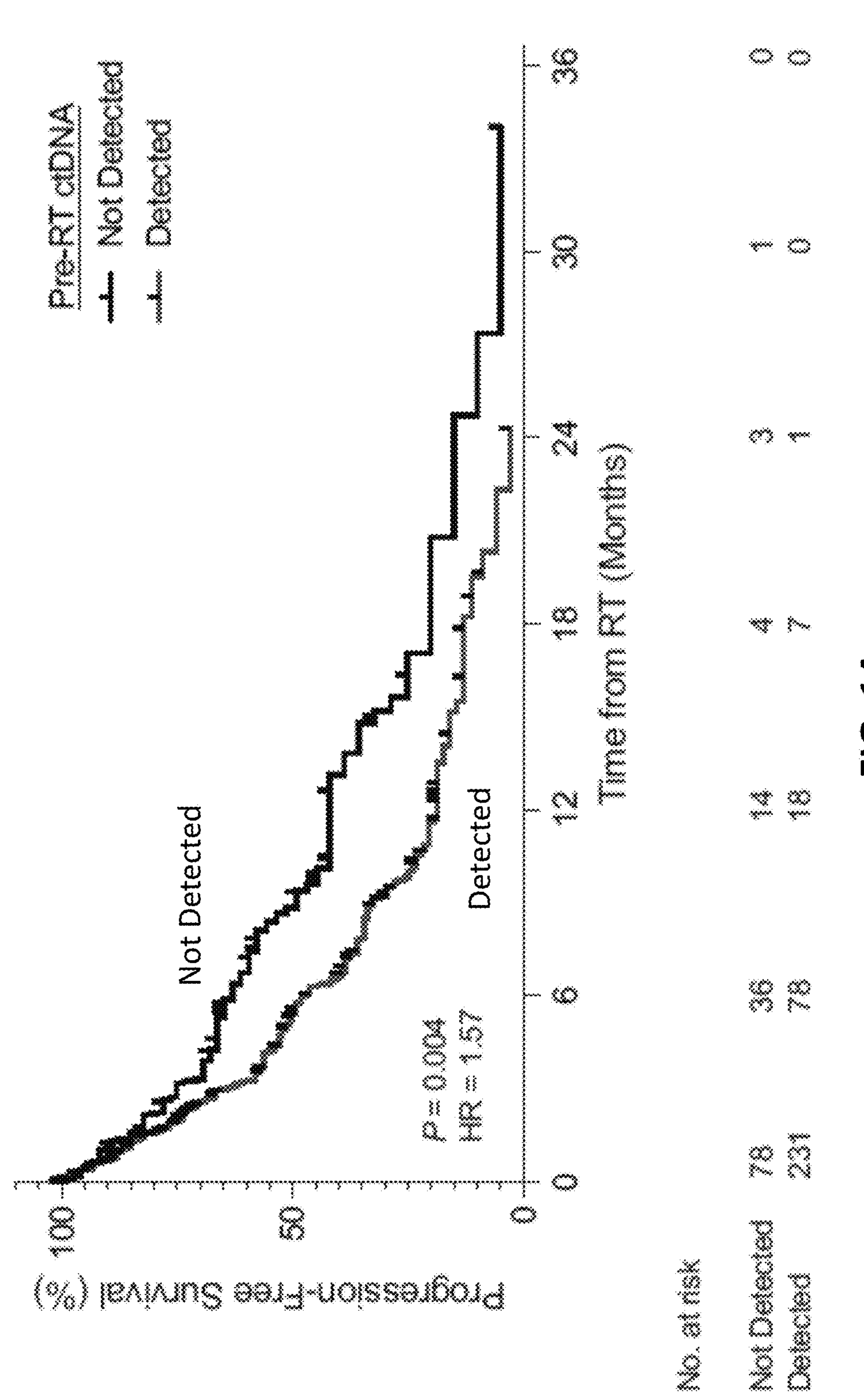
FIG. 1A is a Kaplan-Meier curve demonstrating progression-free survival in oligometastatic NSCLC patients stratified by ctDNA detection prior to radiotherapy. P values were calculated by the log-rank test and HRs by the Mantel-Haenszel method.
Figure 1B:
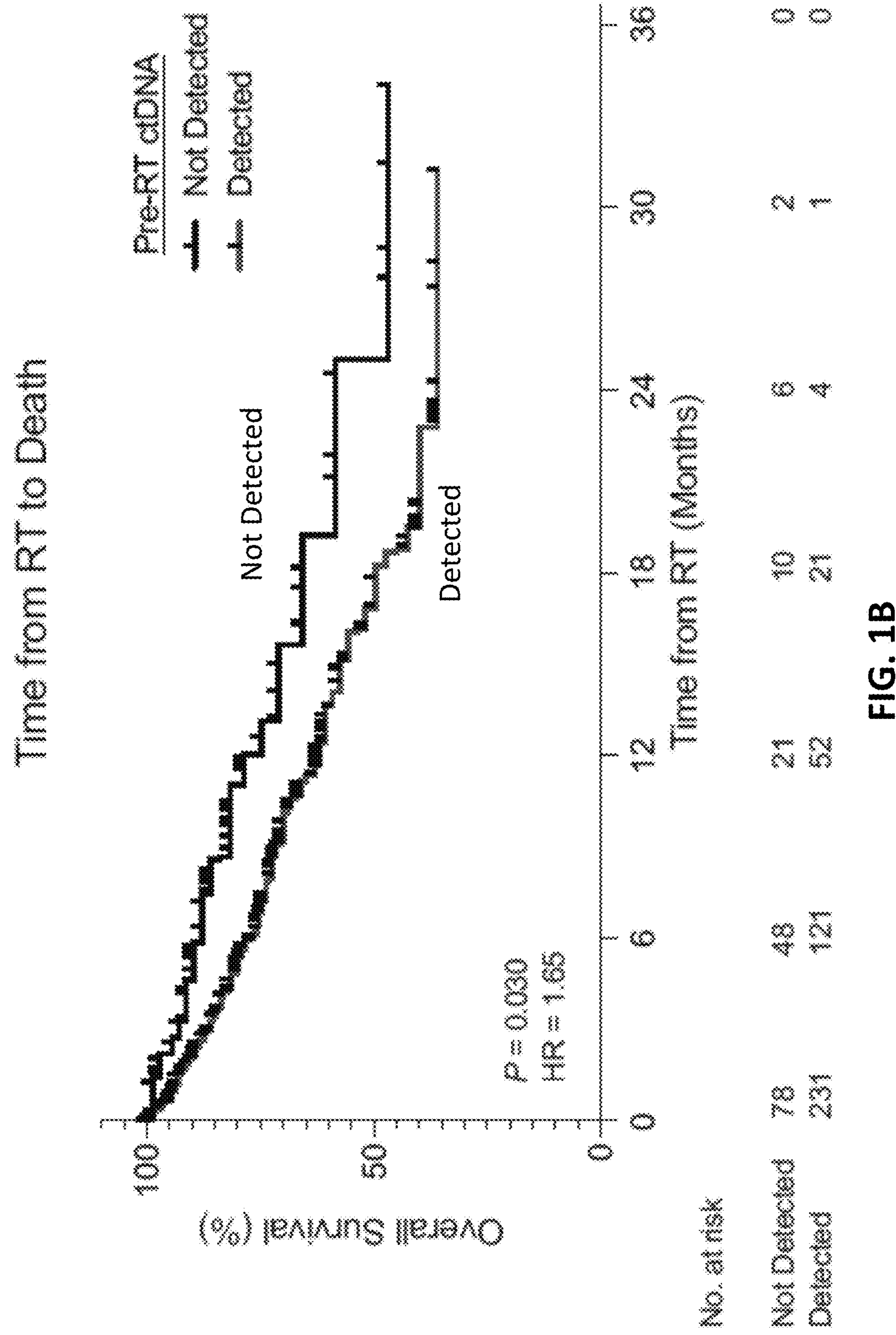
FIG. 1B is a Kaplan-Meier curve demonstrating overall survival in oligometastatic NSCLC patients stratified by ctDNA detection prior to radiotherapy. P values were calculated by the log-rank test and HRs by the Mantel-Haenszel method.

Of the 309 patients who underwent RT after liquid biopsy, 26% (n=79) had zero, 56% (n=175) had 1-3, and 18% (n=55) had ≥4 pathogenic or likely pathogenic variants detected in ctDNA. 151 patients had progressive disease and 34 patients died during the study period. Kaplan-Meier analysis demonstrated significantly worse OS in patients with detectable ctDNA pre-RT compared to those without detectable ctDNA pre-RT (median 16.8 months vs. 25 months; p=0.027, HR=1.65) (FIG. 1B). Patients with detectable ctDNA pre-RT also had significantly worse PFS compared to those with undetectable ctDNA pre-RT (median 5.4 months vs 8.8 months; p=0.021, HR=1.57). Strikingly, we observed that survival could be further risk-stratified granularly by the number of pathogenic ctDNA variants detected pre-RT, with significantly worse PFS (p=0.003) and OS (p=0.045) comparing pre-RT ctDNA with no detectable variants, 1-3 variants, and >4 variants. Multivariate Cox proportional hazards modeling for PFS and OS corroborated these data (PFS HR=1.16, CI 1.06-1.25; OS HR=1.15, CI 1.04-1.24) while being insignificant for other clinical parameters including gender, age at diagnosis, and squamous histology. Additionally, ctDNA levels demonstrated significance with both the mean and maximum ctDNA VAF pre-RT being associated with increased risk of progression and death (mean VAF PFS HR=8.16, CI=1.69-29.20, OS HR=10.2, CI=2.10-37.05; maximum VAF PFS HR=4.4, CI=1.41-11.93, OS HR=5.26, CI=1.63-14.77).

Conclusions

The findings using a large multi-institutional retrospective cohort suggest that ctDNA can serve as a valuable pre-RT biomarker for risk-stratifying oligometastatic NSCLC patients, with the potential to personalize RT versus systemic therapy decision-making.

Example 3-Pre-Radiotherapy ctDNA Liquid Biopsy for Risk Stratification of Oligometastatic Non-Small Cell Lung Cancer Example 3 describes re-radiotherapy ctDNA liquid biopsy for risk stratification of oligometastatic non-small cell lung cancer.

Abstract

The optimal treatment paradigm for patients with oligometastatic non-small cell lung cancer (NSCLC) remains unclear. Some patients with oligometastatic disease experience prolonged remission after locally consolidative radiation therapy (RT), while others harbor micrometastatic disease (below limits of detection by imaging) and benefit from systemic therapy. To risk-stratify and identify the patients most likely to benefit from locally consolidative RT, a multi-institutional cohort study of 1487 patients with oligometastatic NSCLC undergoing liquid biopsy analysis of circulating tumor DNA (ctDNA) was performed. In total, 1880 liquid biopsies were performed and approximately 20% of patients (n=309) had ctDNA measured prior to RT and after their diagnosis of oligometastatic disease. Patients with undetectable ctDNA (pathogenic or likely pathogenic variants in plasma using the Tempus xF assay) before RT had significantly improved progression-free survival (PFS) (P=0.004) and overall survival (OS) (P=0.030). ctDNA maximum variant allele frequency (VAF) pre-RT and ctDNA mutational burden pre-RT were both significantly inversely correlated with PFS (maximum VAF P=0.008, mutational burden P=0.003) and OS (maximum VAF P=0.007, mutational burden P=0.045). These findings were corroborated by multivariate Cox proportional hazards models that included eight additional clinical and genomic parameters. Overall, these data suggest that in patients with oligometastatic NSCLC, pre-RT ctDNA can potentially identify the patients most likely to benefit from locally consolidative RT and experience prolonged PFS and OS. Similarly, ctDNA may be useful to identify undiagnosed micrometastatic disease where it may be appropriate to prioritize systemic therapies.

Introduction

Oligometastatic non-small cell lung cancer (NSCLC) offers a unique opportunity for personalized liquid biopsy-guided therapies. While NSCLC patients with widespread metastatic disease are incurable and generally have poor outcomes, patients with a limited metastatic burden of disease can sometimes achieve prolonged remission after definitive management of the primary tumor and metastatic sites through a combination of systemic agents and local consolidative therapies such as RT.

However, identifying patients who have truly oligometastatic disease and are most likely to benefit from locally consolidative radiation therapy is challenging. Many patients with perceived oligometastatic NSCLC on imaging likely harbor undetected widespread metastatic disease (micrometastatic disease) below the limit of detection of current imaging technologies. Establishing a new liquid biopsy biomarker to segregate those patients with truly oligometastatic disease from those with widespread micrometastatic disease could alter treatment approaches. Patients with evidence of micrometastatic disease could be triaged to earlier systemic therapies or enrollment in clinical trials—in addition to sparing the costs, systemic therapy breaks, and potential side effects associated with local consolidative therapies. Similarly, clinicians could provide more concrete guidance to patients regarding the possibility of prolonged remission, and potentially offer more aggressive locally consolidative treatment in truly oligometastatic patients who do not harbor liquid biopsy evidence of micrometastatic disease.

It has been previously shown that post-RT plasma circulating tumor DNA (ctDNA) is powerfully prognostic in localized NSCLC. Here, it was hypothesized that ctDNA analysis could be applied earlier (pre-RT) to risk-stratify patients with oligometastatic NSCLC and enable patient-personalized determination of local consolidative radiotherapy versus systemic therapy.

Analysis of ctDNA

The median follow-up time after initial blood collection for liquid biopsy analysis was 10.3 months. Across all ctDNA assays, 3503 pathogenic or likely pathogenic variants were identified (1.8 variants/sample, mean). Of the sub-cohort of 309 patients who underwent liquid biopsy after the diagnosis of oligometastatic disease and before RT, 48% (n=151) experienced progressive disease and 11% (n=34) died during the study period. ctDNA quantitation was based on the detection of pathogenic or likely pathogenic variants in plasma. ctDNA was detected in 74% of oligometastatic NSCLC patients prior to RT (n=230) while the remaining 26% (n=79) had no detectable ctDNA pre-RT. Among the 230 ctDNA-detectable patients, 76% (n=175) had 1-3 variants, while the remainder (n=55) had >4 pathogenic or likely pathogenic variants present.

Figure 2A:
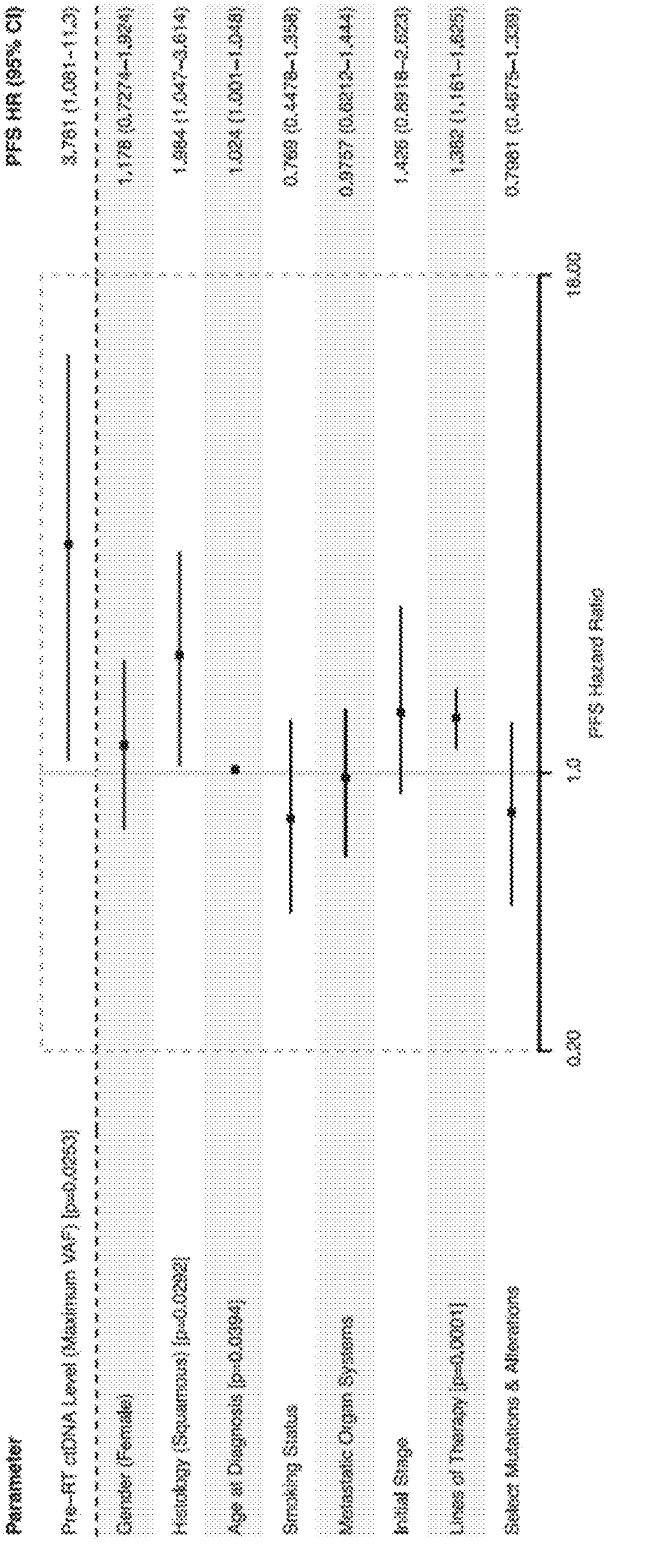
FIG. 2A is a plot of multivariate Cox regression modeling performed for progression-free survival with parameters including the maximum ctDNA variant allele frequency (VAF) prior to radiotherapy, as well as clinically relevant covariates. Driver gene alterations include those defined in FIGS. 3 and 4.
Figure 2B:
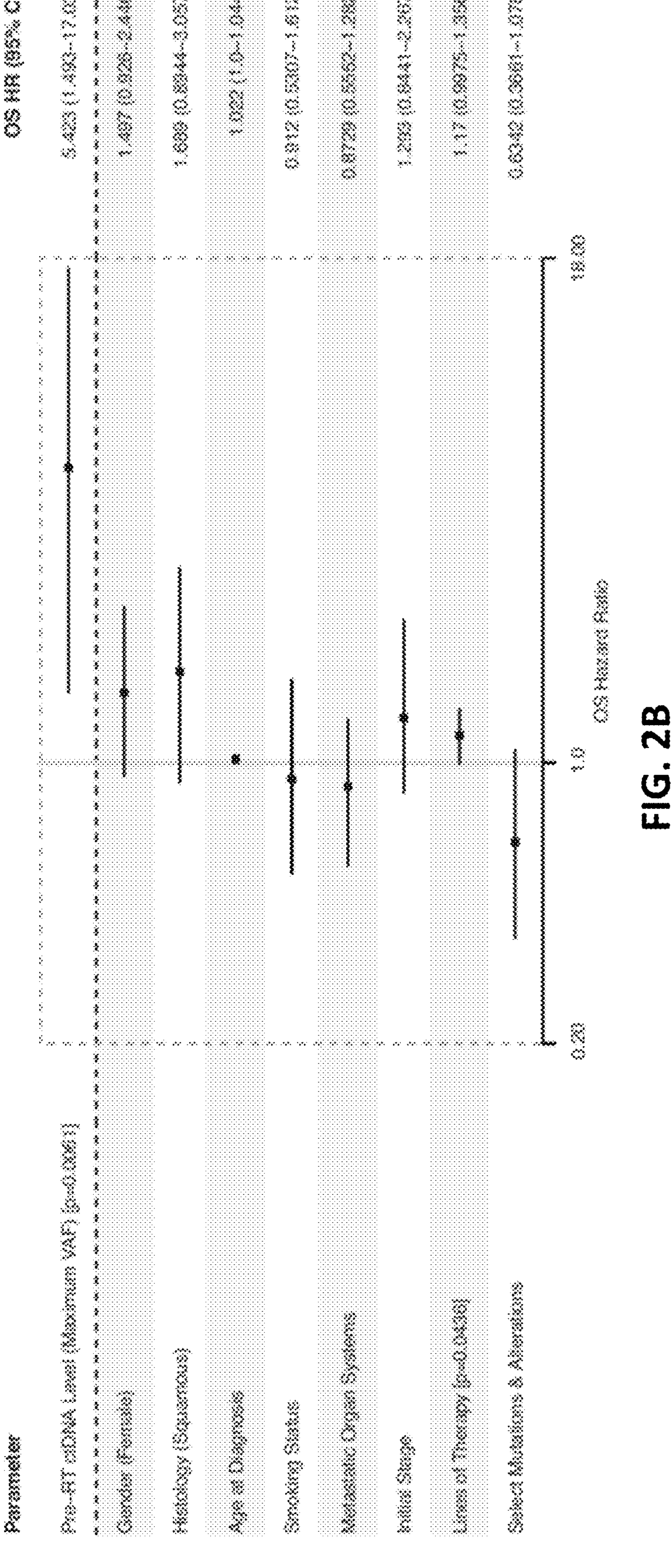
FIG. 2B is a plot of multivariate Cox regression modeling performed for overall survival with parameters including the maximum ctDNA variant allele frequency (VAF) prior to radiotherapy, as well as clinically relevant covariates. Driver gene alterations include those defined in FIGS. 3 and 4.
Figure 5A:
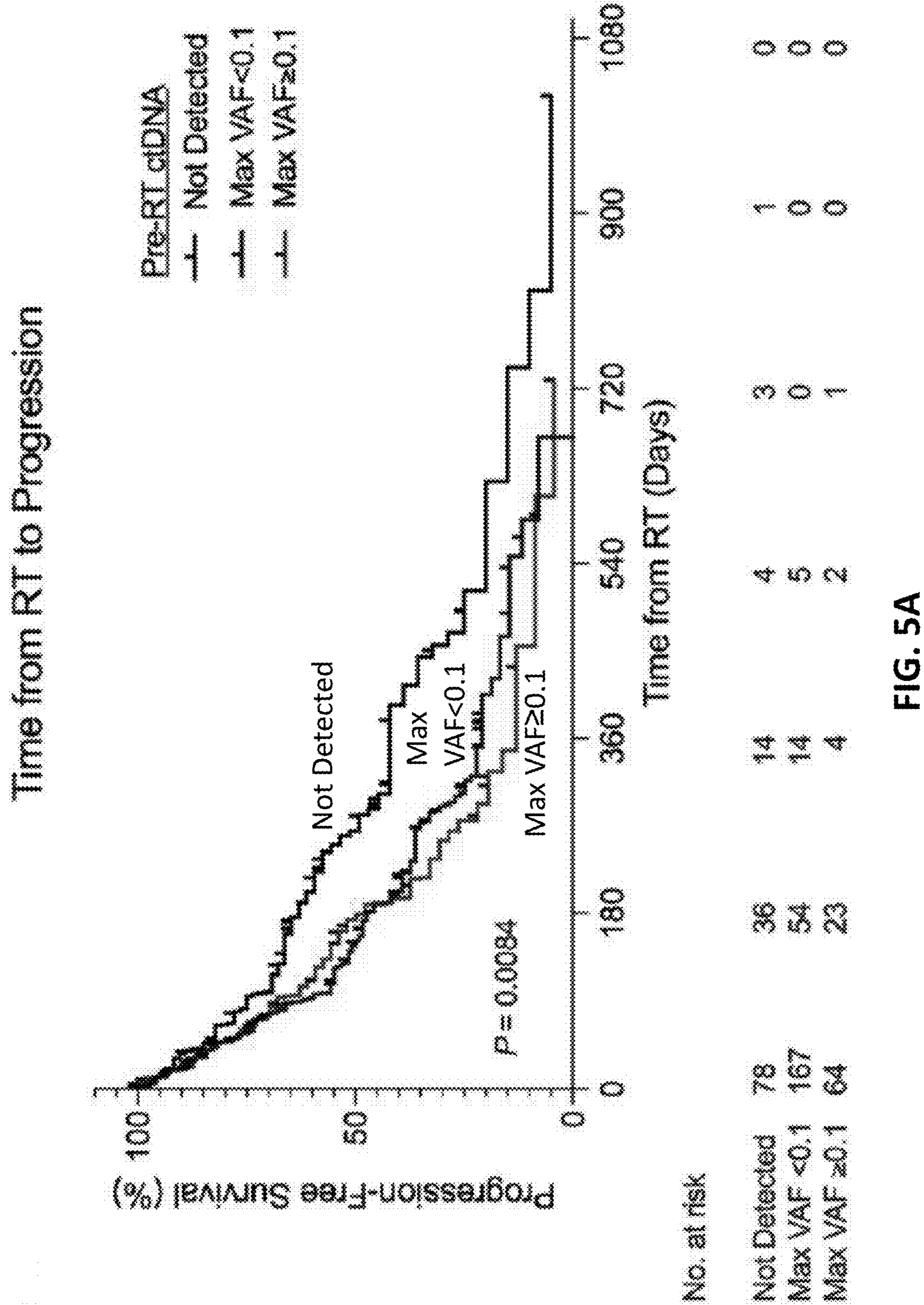
FIG. 5A is a Kaplan-Meier curve demonstrating progression-free survival in oligometastatic NSCLC patients stratified by pre-radiotherapy ctDNA maximum variant allele frequency (VAF) levels. P values were calculated by the log-rank test for trend.
Figure 5B:
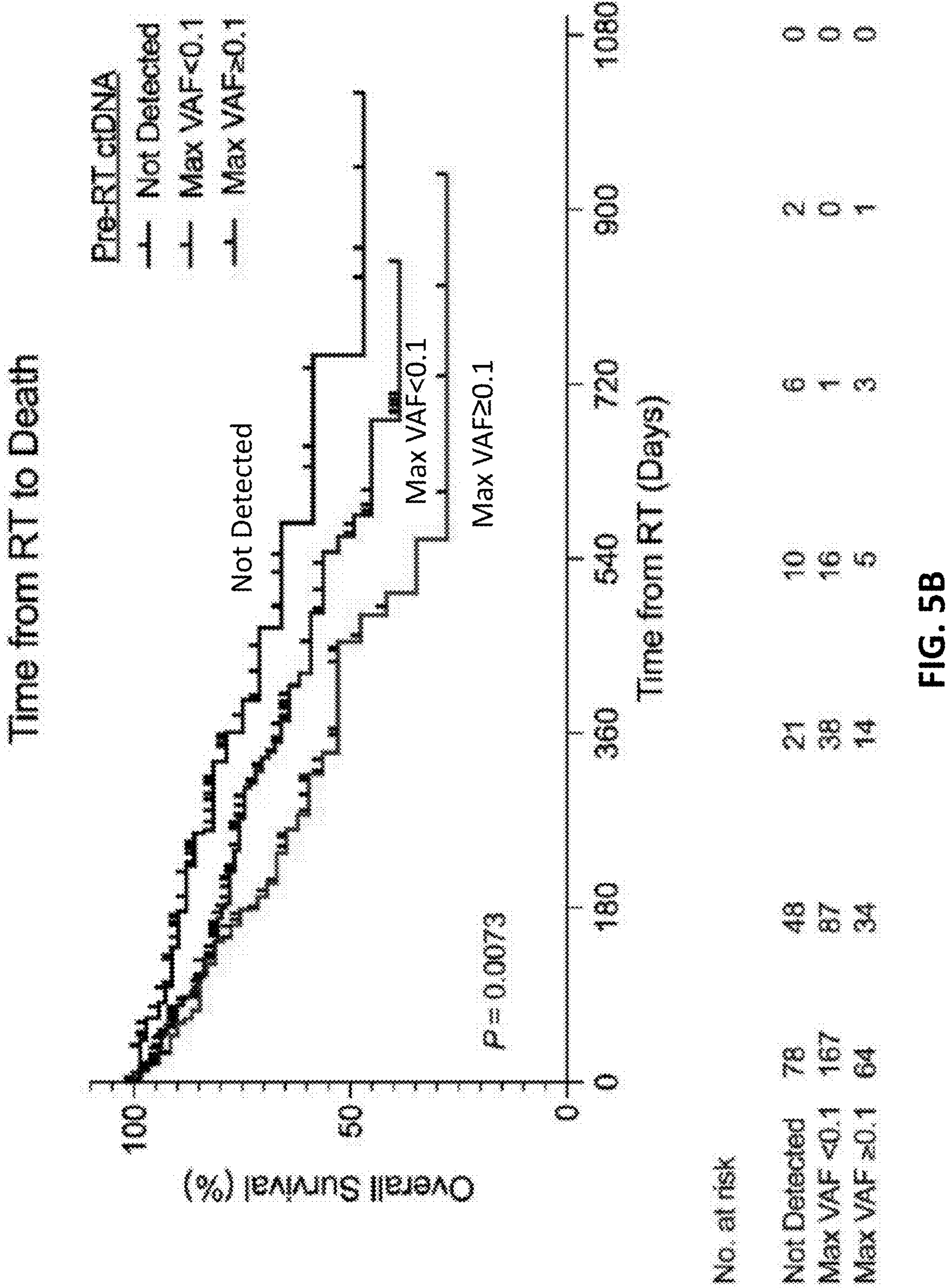
FIG. 5B is a Kaplan-Meier curve demonstrating overall survival in oligometastatic NSCLC patients stratified by pre-radiotherapy ctDNA maximum variant allele frequency (VAF) levels. P values were calculated by the log-rank test for trend.

Both progression-free survival (PFS) and overall survival (OS) were significantly worse in oligometastatic NSCLC patients with detectable ctDNA from pre-RT liquid biopsies, as compared to those without detectable ctDNA pre-RT. Patients with detectable ctDNA pre-RT had a median PFS of 5.4 months versus 8.8 months (p=0.004, hazard ratio [HR] =1.57, confidence interval [CI]=1.15-2.13) (FIG. 1A). Similar findings were observed for overall survival, with a median OS of 16.8 months versus 25 months (p=0.030, HR=1.65, CI=1.05-2.61) (FIG. 1B).

ctDNA levels (defined by the variant allele frequency) demonstrated significant risk correlations, with the maximum pre-RT ctDNA VAF associated with increased risk of both disease progression (p=0.008) and death (p=0.007) (FIGS. 5A and 5B). These findings were corroborated by multivariate Cox proportional hazards models for PFS (p=0.025, HR=3.78, CI=1.08-11.30) (FIG. 2A) and OS (p=0.006, HR=5.42, CI=1.49-17.03) (FIG. 2B). Notably, beyond pre-RT ctDNA levels, multivariate Cox modeling of OS only showed significant impacts from the lines of therapy a patient received (p=0.044), while for PFS, squamous histology and age at diagnosis also demonstrated significance. Other clinical and genomic parameters including gender, smoking status, metastatic burden, initial disease stage, and presence of known common mutations and alterations were not significant with regard to survival outcomes.

Figure 6A:
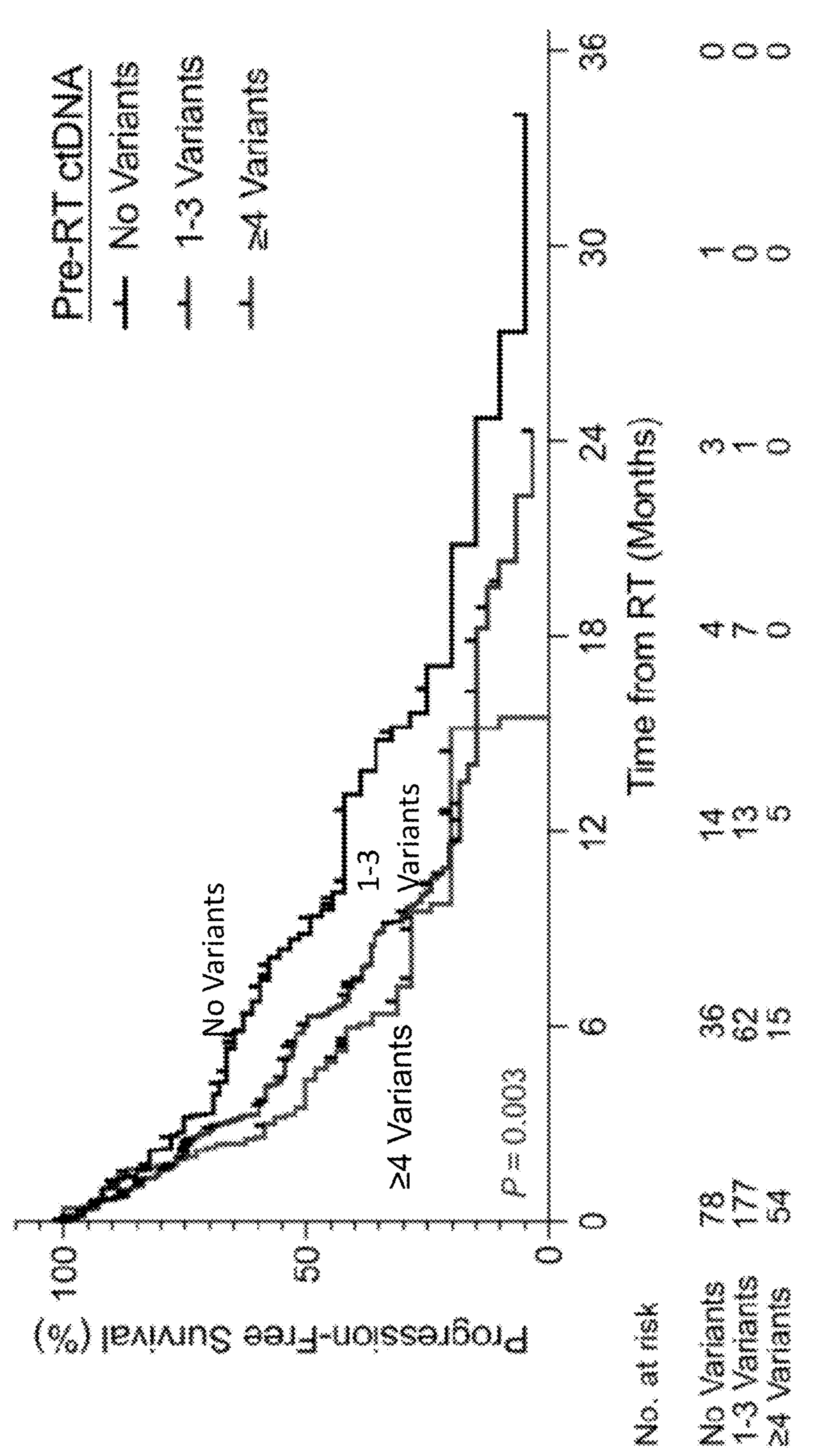
FIG. 6A is a Kaplan-Meier curve demonstrating progression-free survival in oligometastatic NSCLC patients stratified by pre-radiotherapy ctDNA mutational burden. P values were calculated by the log-rank test for trend.
Figure 6B:
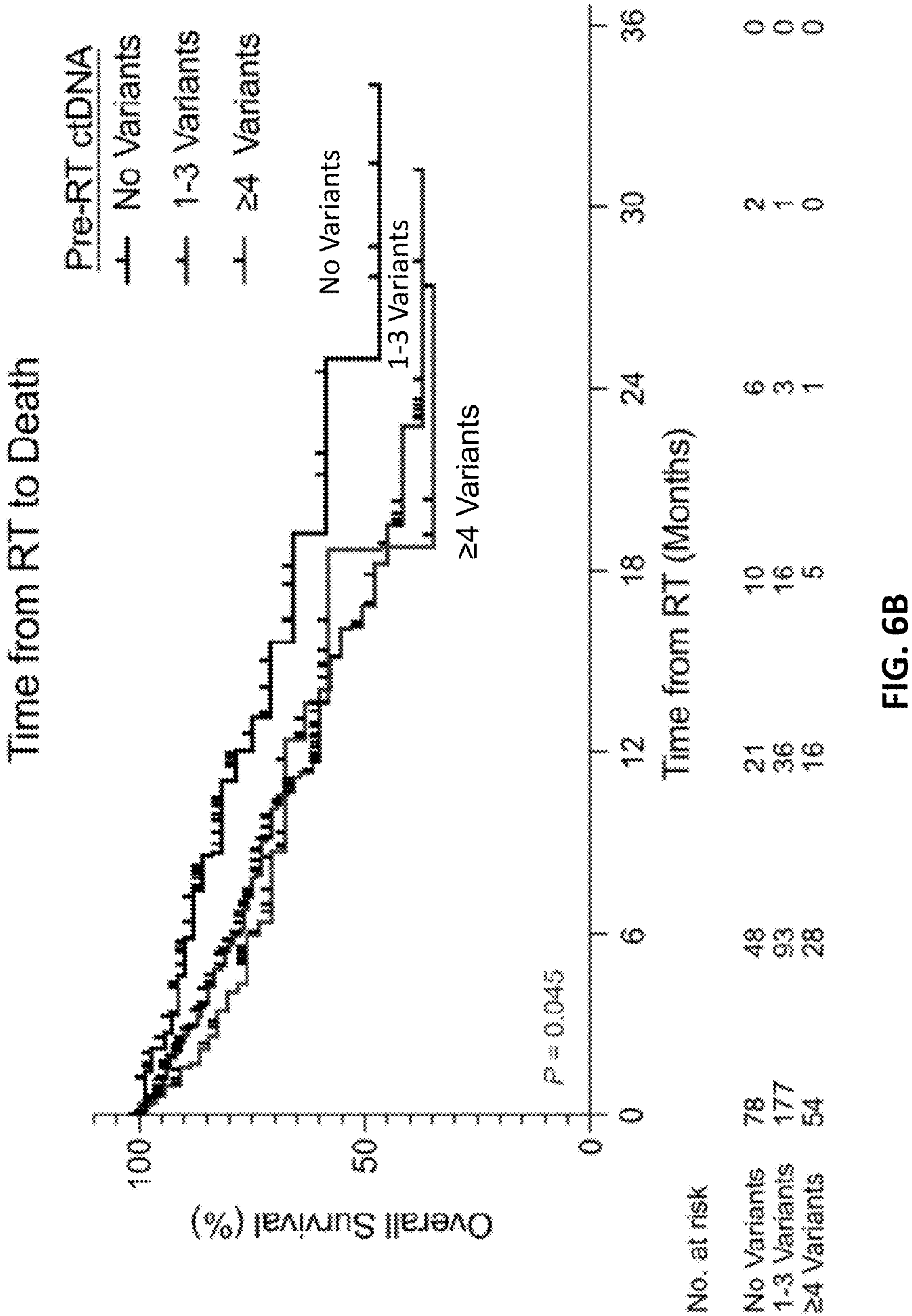
FIG. 6B is a Kaplan-Meier curve demonstrating overall survival in oligometastatic NSCLC patients stratified by pre-radiotherapy ctDNA mutational burden. P values were calculated by the log-rank test for trend.
Figure 7A:
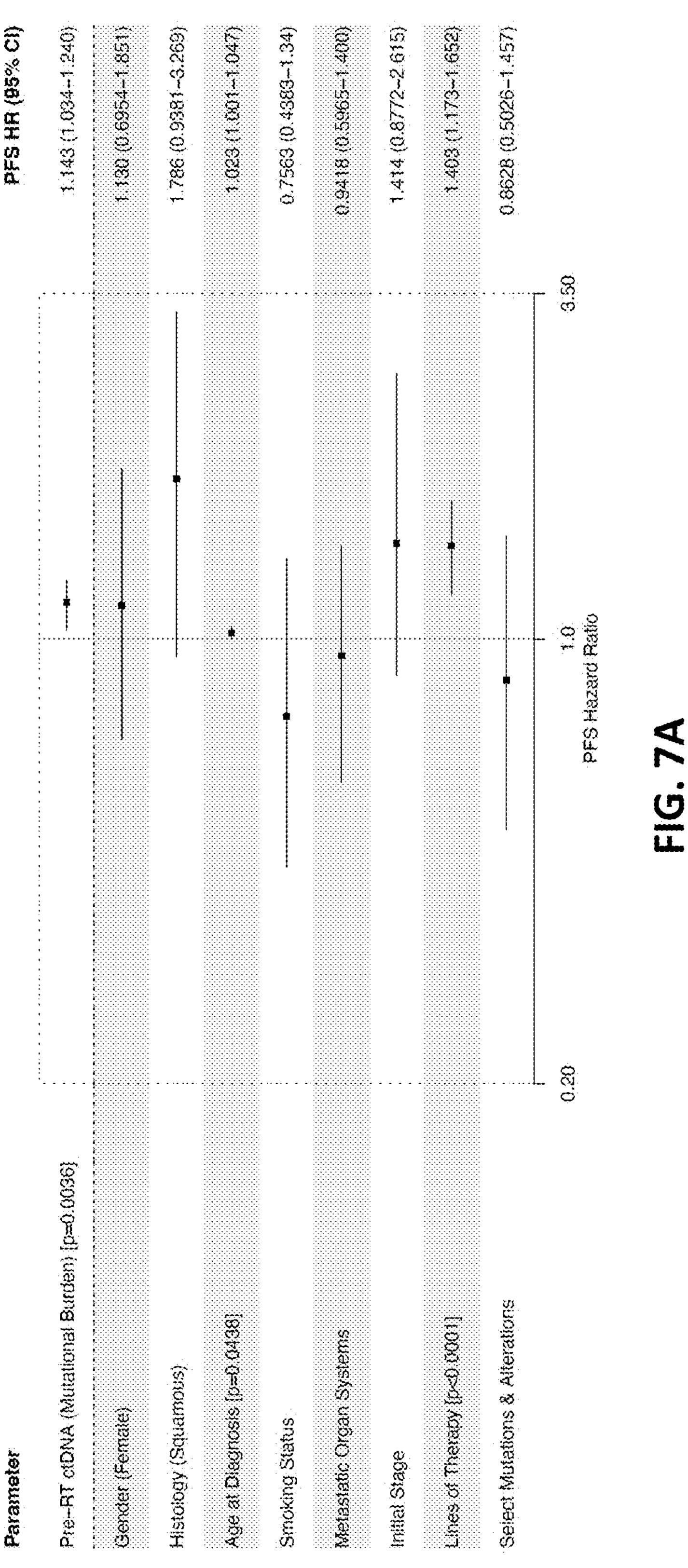
FIG. 7A is a table of multivariate Cox regression modeling performed for progression-free survival with parameters including the number of detected mutations in ctDNA (mutational burden) prior to radiotherapy, as well as clinically relevant covariates. Driver gene alterations include those defined in FIGS. 3 and 4.
Figure 7B:
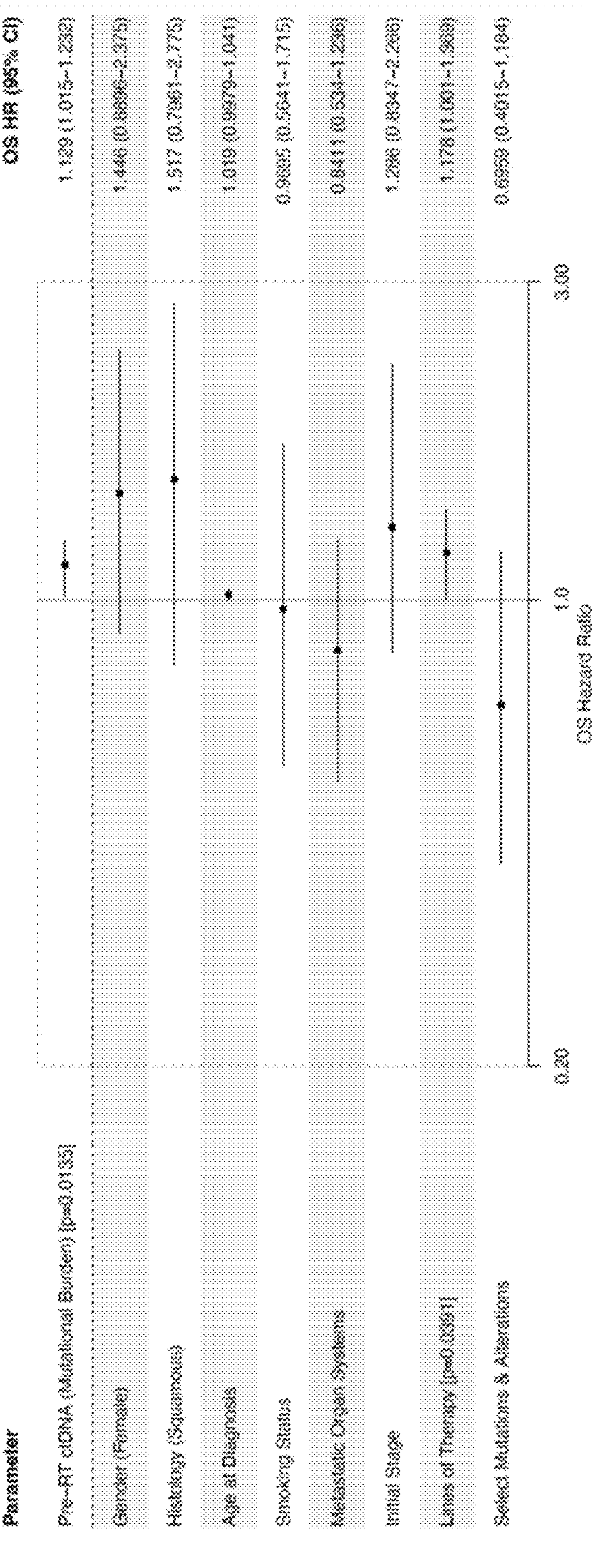
FIG. 7B is a table of multivariate Cox regression modeling performed for overall survival with parameters including the number of detected mutations in ctDNA (mutational burden) prior to radiotherapy, as well as clinically relevant covariates. Driver gene alterations include those defined in FIGS. 3 and 4.

Similar findings were observed when stratifying patients by pre-RT ctDNA mutational burden (the number of detectable pathogenic or likely pathogenic variants detected in plasma), with increasing ctDNA mutational burden associated with both progression (p=0.003) and death (p=0.045) (FIGS. 6A and 6B). These findings were again corroborated by multivariate Cox proportional hazards models for both PFS (p=0.004, HR=1.14, CI=1.03-1.24) (FIG. 7A) and OS (p=0.014, HR=1.13, CI=1.02-1.23) (FIG. 7B). Beyond pre-RT ctDNA mutational burden, number of lines of therapy a patient received was again significant for OS on multivariate analysis (p=0.039), while other clinical and genomic parameters were not.

Translational Implications

The definition of the oligometastatic disease state has remained frustratingly subjective since its original proposal in 1995 by Hellman and Weichselbaum. Locally focused treatment for disease control was initially only considered in select NSCLC patients with a solitary metastasis in either the brain or adrenal gland. More recently, phase 2 studies in patients with up to 3 or 5 metastatic lesions have shown improved survival outcomes when treated with locally ablative radiotherapy. Current trials are now testing whether this radiation-oriented paradigm may also benefit patients with even greater numbers of metastatic lesions, highlighting the need for more precise patient selection approaches. Example 3 suggests that a pre-RT ctDNA liquid biopsy could serve as the first precision biomarker to objectively redefine oligometastatic disease, which would empower oncologists to provide more concrete advice to patients regarding RT for disease control and enable prioritization of systemic therapy for patients with ctDNA evidence of aggressive micrometastatic disease.

Indeed, this study represents the largest ever real-world analysis of liquid biopsies in oligometastatic NSCLC, leveraging a multi-institutional dataset of 1487 patients who underwent 1880 liquid biopsies. The analysis reveals that ctDNA testing performed pre-RT can risk-stratify those patients with truly oligometastatic NSCLC from those who likely harbor widespread micrometastatic disease (below current imaging limits of detection). The modeling shows that the risk of disease progression and survival are informed by ctDNA quantitation, whether by mutational burden or the overall amount of ctDNA represented by VAF.

Figure 8:
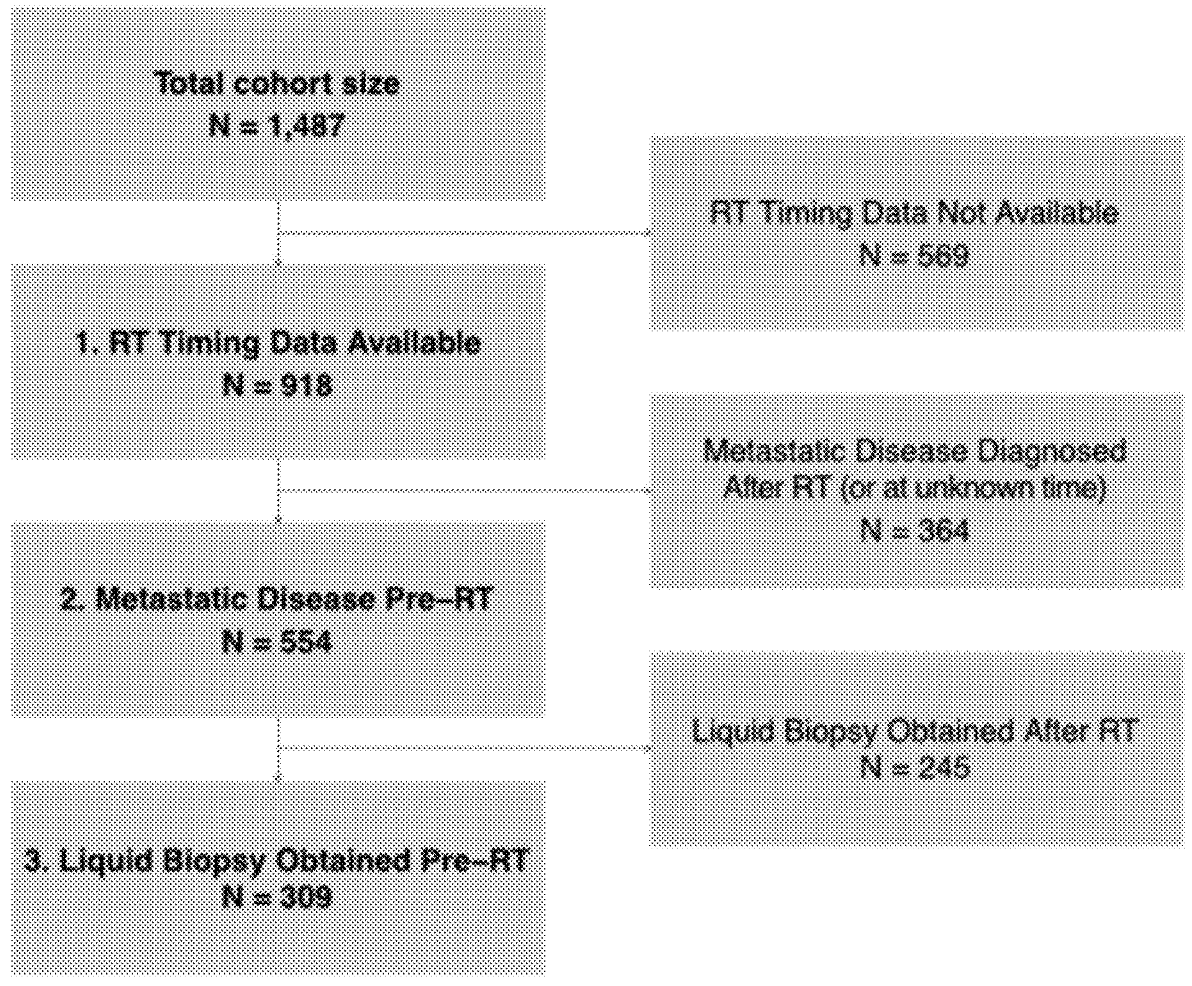
FIG. 8 is a schematic diagram of a process of patient selection used in the examples herein. A sub-cohort was selected from the total patient population (n=1,487) based on the available clinical data. Patients were selected for the sub-cohort if data on the timing of RT was available, data on the time that metastatic disease was diagnosed was available indicating that metastatic disease was diagnosed prior to RT, and a liquid biopsy was performed prior to the initiation of RT.
Figure 9A:
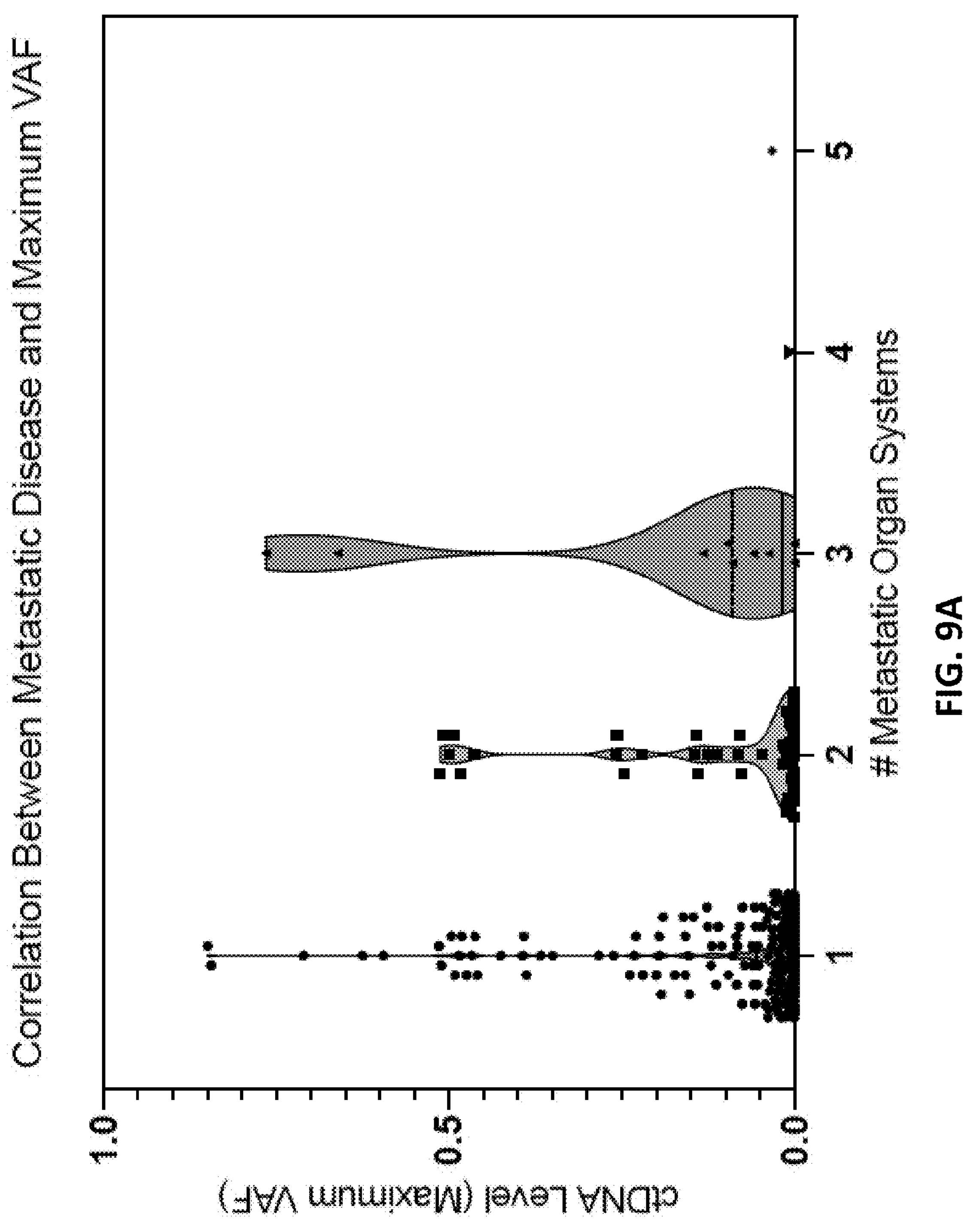
FIG. 9A is a graph of a correlative analysis between pre-RT ctDNA and metastatic burden (represented by the number of metastatic organ systems). No significant correlation was identified between the pre-RT ctDNA level and maximum VAF (one-way ANOVA P=0.16, R2=0.015).

This approach should be prospectively evaluated in a clinical trial that redefines oligometastatic NSCLC to include a discrete liquid biopsy metric encompassing a low or undetectable ctDNA level. This technique may also be valuable for those patients who undergo curative-intent treatment for earlier stages of NSCLC, but subsequently develop oligometastatic disease (deemed "oligorecurrence") and are weighing individualized treatment decisions. A sub-cohort where a liquid biopsy was definitively performed prior to RT administration in oligometastatic NSCLC patients was explicitly focused on (FIG. 8). Notably, ctDNA levels did not correlate with metastatic burden (FIGS. 9A and 9B). This finding, combined with the fact that ctDNA correlated significantly with OS and PFS, suggests that ctDNA may more objectively reflect disease burden, aggressiveness, and underlying biology than classic imaging-based approaches to determining metastatic burden.

Radiation therapy plans were determined by individual clinicians and did not necessarily target all metastatic sites. Although this practice introduces clinical heterogeneity into the dataset, it may also more accurately capture real-world clinical practice patterns and suggests a broader extensibility of our clinical-correlative liquid biopsy findings. Moreover, the significant PFS data was corroborated by similarly significant OS data in this real-world cohort.

In conclusion, this study suggests that pre-RT ctDNA may be a powerful biomarker to accurately identify micrometastatic disease in patients with oligometastatic NSCLC. Earlier risk stratification using this liquid biopsy biomarker could support future clinical trials to enable personalized decision-making based on per-patient ctDNA risk profiles. Patients with high-risk ctDNA profiles could undergo systemic therapy prioritization and potentially escalation (avoiding systemic therapy breaks related to RT and potential RT toxicities), while patients with undetectable ctDNA or low ctDNA risk profiles could be offered locally consolidative stereotactic radiotherapy with biomarker-driven confidence.

Methods

All analyses were performed using de-identified patient data. The study was exempt from institutional review board evaluation and informed consent given the de-identified nature of the data.

Cohort Selection

Figure 10A:
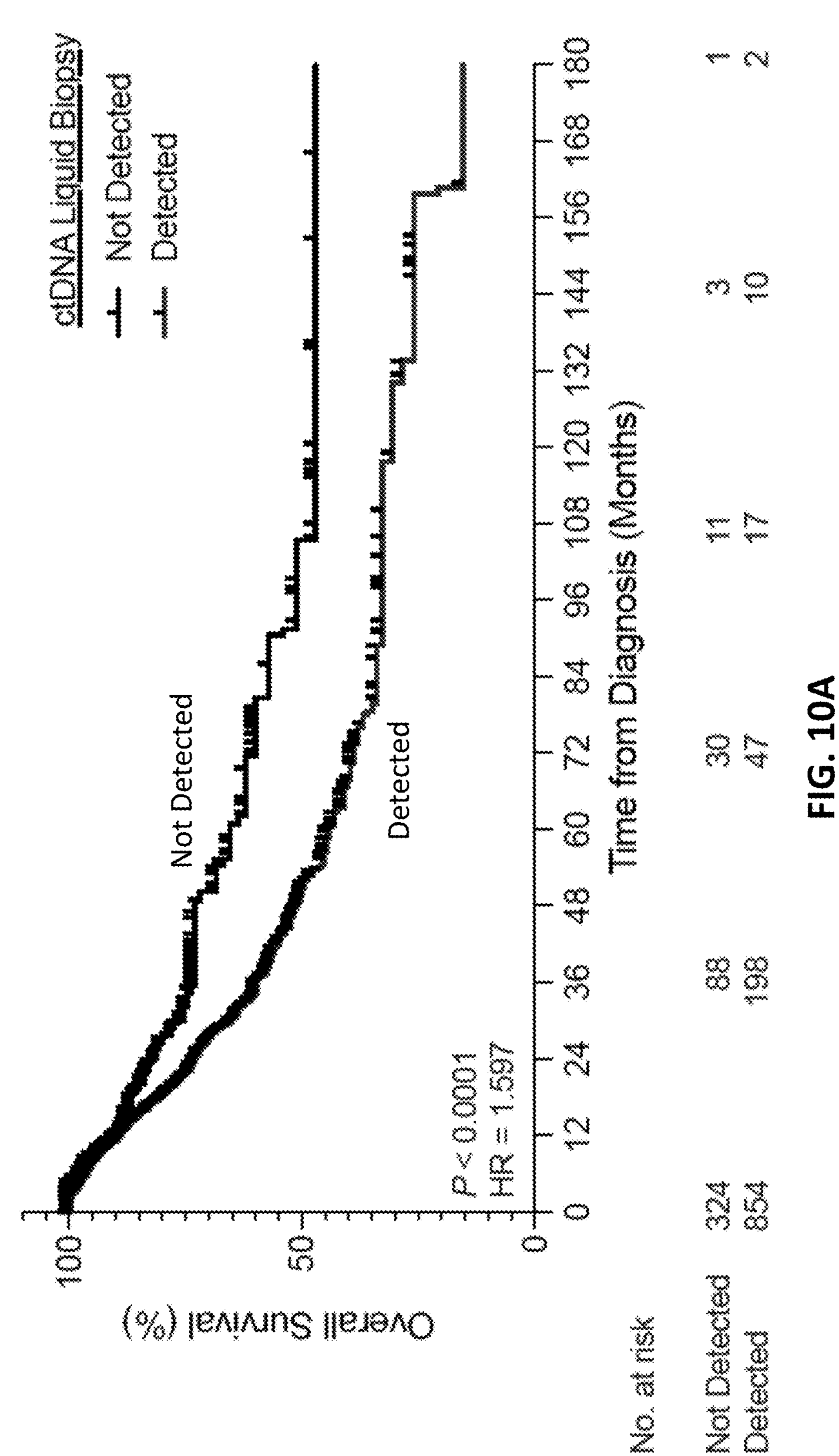
FIG. 10A is a Kaplan-Meier curve of a survival analysis on the patients excluded from the sub-cohort (a total of n=1,178), where complete data on the timing of RT and metastatic disease were not available. If multiple liquid biopsies were available for a given patient, the earliest timepoint was selected. Kaplan-Meier curves reassuringly demonstrated significant differences in overall survival in oligometastatic NSCLC patients stratified by ctDNA detection levels. P values were calculated by the log-rank test and HR by the Mantel-Haenszel method.
Figure 10B:
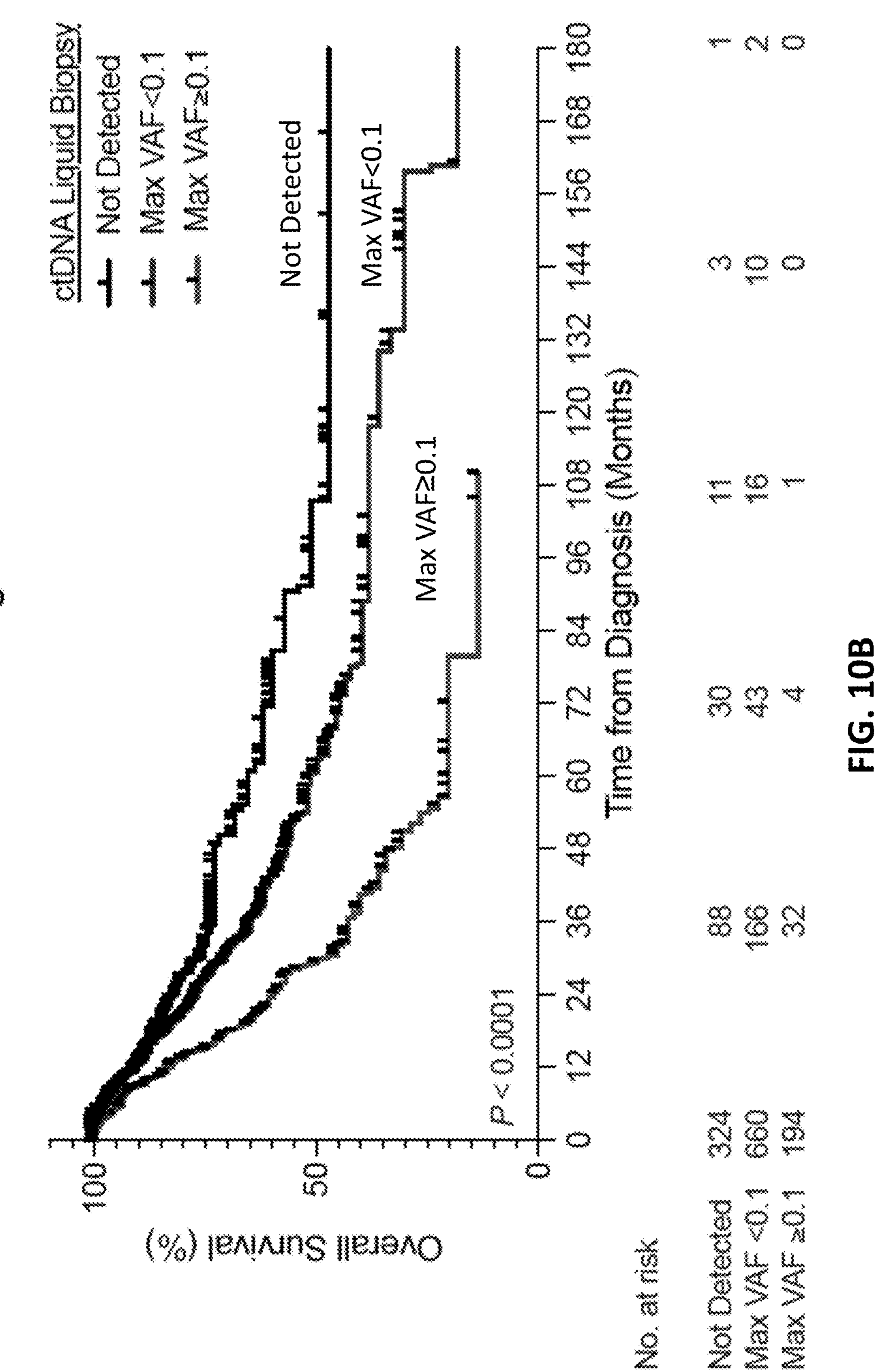
FIG. 10B is a Kaplan-Meier curve of a survival analysis on the patients excluded from the sub-cohort (a total of n=1,178), where complete data on the timing of RT and metastatic disease were not available. If multiple liquid biopsies were available for a given patient, the earliest timepoint was selected. Kaplan-Meier curves reassuringly demonstrated significant differences in overall survival in oligometastatic NSCLC patients stratified by ctDNA VAF levels. P values were calculated by the log-rank test and HR by the Mantel-Haenszel method.

A multi-institutional real-world cohort consisting of 1487 patients from both academic and community practices who were diagnosed with oligometastatic NSCLC was leveraged. Peripheral blood samples were collected for liquid biopsy analysis between 2016 and 2022. The cohort mean age (SD) was 64.7 years (10.1), with similar numbers of male and female patients (784 female [53%], 703 male [47%]) (FIG. 3). Approximately 73% of the patients had adenocarcinoma, 18% had squamous cell carcinoma, and 9% did not have histological subtyping available or had another subtype of NSCLC. Every patient underwent liquid biopsy and ctDNA analysis using the Tempus XF assay at different time points, for a total of 1880 ctDNA assays (FIG. 4). All patients were reported by the treating physicians to have metastatic disease; a cohort was sub-selected for this analysis where a ctDNA liquid biopsy was definitively obtained after the diagnosis of oligometastatic disease but prior to radiotherapy (n=309 patients) (FIG. 8). To control for selection bias, a repeat analysis of all patients excluded from the sub-cohort (n=1178) was performed (FIGS. 10A and 10B), that demonstrated similarly significant findings of OS and PFS stratified by ctDNA results. The sub-cohort was selected for this analysis to avoid making assumptions about liquid biopsy timing.

Liquid Biopsy

The Tempus XF liquid biopsy assay is a laboratory-developed test (LDT) designed to detect oncogenic and resistance mutations in cell-free DNA. The assay detects single nucleotide variants (SNVs), insertions/deletions (indels), rearrangements, copy number variations (CNVs), and microsatellite instability (MSI) with high sensitivity and specificity. ctDNA results were analyzed for variants using VarDict and characterized as pathogenic or likely pathogenic based on their predicted functional impact as determined by SnpEff and clinical evidence, following the ACMG/AMP guidelines for variant classification. Variants considered benign, likely benign, or having conflicting evidence were excluded. Variants were quantified per patient, along with the maximum variant allele frequency (VAF). Fusions and CNVs were identified using SpeedSeq and CNVkit, respectively. Patient-level data of time to outcomes, ctDNA mutational burden, VAF, and other parameters used in this study were determined.

Statistical Analysis

Median follow-up time was determined using the reverse Kaplan-Meier method. Outcomes for overall survival (OS) and progression-free survival (PFS) were both calculated from the start of RT (i.e., time from RT to death and time from RT to progression). Progression was reported by the managing clinicians. Kaplan-Meier curve p-values represent the log-rank test. Hazard ratios for OS and PFS in Kaplan-Meier analyses reflect the Mantel-Haenszel test. Multivariate Cox regression p-values were calculated using the Wald test. Data were managed using Apache Superset 2.1.0, and statistical analyses were performed using GraphPad Prism version 9.5.1 and R version 4.2.2.

What is claimed is:

1. A method of selecting a treatment for an early-stage non-small cell lung cancer (NSCLS) for a patient in need, the method comprising:

a. providing a blood sample from the patient in need prior to radiation therapy (RT);

b. subjecting the blood sample to a liquid biopsy assay configured to detect at least one circulating tumor DNA (ctDNA) variant indicative of oligometastatic (NSCLS) disease; and c. selecting and administering a systemic therapy as a treatment if the liquid biopsy assay identifies the at least one ctDNA variant and otherwise selecting and administering a radiation therapy as the treatment.

2. The method of claim 1, wherein the at least one circulating tumor DNA (ctDNA) variant indicative of oligometastatic (NSCLS) disease is selected from an oncogenic mutation variant, a resistance mutation variant, and any combination thereof.

3. The method of claim 2, wherein the at least one oncogenic mutation variant, resistance mutation variant, and any combination thereof is selected from a single nucleotide variant (SNVs), an insertion/deletion (indel), a rearrangement, a copy number variation (CNV), and a microsatellite instability (MSI).

4. The method of claim 1, wherein the at least one circulating tumor DNA (ctDNA) variant is identified within at least one gene selected from EGFR, ALK, ROS1, MET, RET, BRAF, KRAS, ERBB2, and any combination thereof.

5. The method of claim 1, the method further comprising quantifying the maximum variant allele frequency (VAF) in the patient based on the at least one circulating tumor DNA (ctDNA) variant detected by the liquid biopsy assay.

6. A method of selecting a treatment for an early-stage non-small cell lung cancer (NSCLS) for a patient in need, the method comprising:

a. providing a blood sample from the patient in need prior to radiation therapy (RT);

b. subjecting the blood sample to a liquid biopsy assay configured to detect at least one circulating tumor DNA (ctDNA) variant indicative of oligometastatic (NSCLS) disease;

c. quantifying a maximum variant allele frequency (VAF) in the patient based on the at least one circulating tumor DNA (ctDNA) variant detected by the liquid biopsy assay based on the at least one circulating tumor DNA (ctDNA) variant identified by the liquid biopsy assay; and d. selecting and administering a systemic therapy as a treatment if the maximum VAF value falls above a threshold VAF value and otherwise selecting and administering a radiation therapy as the treatment.

7. The method of claim 6, wherein the threshold maximum VAF value is zero.

8. The method of claim 7, wherein the threshold maximum VAF value is 0.1.

9. The method of claim 6, wherein the at least one circulating tumor DNA (ctDNA) variant indicative of oligometastatic (NSCLS) disease is selected from an oncogenic mutation variant, a resistance mutation variant, and any combination thereof.

10. The method of claim 9, wherein the at least one oncogenic mutation variant, resistance mutation variant, and any combination thereof is selected from a single nucleotide variant (SNVs), an insertion/deletion (indel), a rearrangement, a copy number variation (CNV), and a microsatellite instability (MSI).

11. The method of claim 10, wherein the at least one variant is identified within a gene selected from EGFR, ALK, ROS1, MET, RET, BRAF, KRAS, ERBB2, and any combination thereof.

* * * * *